US007833933B2

(12) United States Patent
Herbst et al.

(10) Patent No.: US 7,833,933 B2
(45) Date of Patent: Nov. 16, 2010

(54) PROCESS FOR THE PREPARATION OF A PARAFFIN ISOMERIZATION CATALYST

(75) Inventors: Konrad Herbst, Kgs. Lyngby (DK); Peter Stern, Virum (DK); Niels Jørgen Blom, Hillerød (DK); Glen Starch-Hytoft, Copenhagen Ø (DK); Kim Grøn Knudsen, Hellerup (DK)

(73) Assignee: Haldor Topsøe A/S, Lyngby (DK)

( * ) Notice: Subject to any disclaimer, the term of this patent is extended or adjusted under 35 U.S.C. 154(b) by 1159 days.

(21) Appl. No.: 11/486,056

(22) Filed: Jul. 14, 2006

(65) Prior Publication Data

US 2007/0123745 A1 May 31, 2007

Related U.S. Application Data

(63) Continuation-in-part of application No. 11/287,206, filed on Nov. 28, 2005, now abandoned.

(51) Int. Cl.
*B01J 23/00* (2006.01)
*B01J 21/00* (2006.01)
*B01J 20/00* (2006.01)

(52) U.S. Cl. ................ 502/327; 502/104; 502/109; 502/308; 502/314; 502/332; 502/333; 502/334; 502/339; 502/349; 502/355; 502/415; 502/439

(58) Field of Classification Search ........... 502/104, 502/109, 308, 314, 327, 332, 333, 334, 339, 502/349, 355, 415, 439
See application file for complete search history.

(56) References Cited

U.S. PATENT DOCUMENTS 4,891,348 A * 1/1990 Imanari et al. ............ 502/309

| 5,422,327 | A |   | 6/1995 | Soled et al. |
|---|---|---|---|---|
| 5,453,556 | A | * | 9/1995 | Chang et al. ............ 585/524 |
| 5,510,309 | A |   | 4/1996 | Chang et al. |
| 5,608,133 | A | * | 3/1997 | Chang et al. ............ 585/524 |
| 5,648,589 | A |   | 7/1997 | Soled et al. |
| 5,710,089 | A | * | 1/1998 | Khare ...................... 502/407 |

(Continued)

OTHER PUBLICATIONS

E. Inglesia, et al., "Selective Isomerization of Alkanes on Supported Tungsten Oxide Acids," 11th National Congress on Catalysis, Studies in Surface Science and Catalysis, vol. 101, 1996, pp. 533-542.

(Continued)

*Primary Examiner*—Cam N Nguyen
(74) *Attorney, Agent, or Firm*—Dickstein Shapiro LLP

(57) ABSTRACT

A process for preparation of a paraffin isomerization catalyst comprising a mixture of a Group IVB metal oxide, a Group VIB metal oxide, a Group IIIA metal oxide and a Group VIII metal. The process includes the steps of: a) contacting a hydroxide of the Group IVB metal with an aqueous solution of an oxyanion of the Group VIB metal to provide a mixture, (b) drying the mixture to provide a dry powder, (c) kneading the powder with a Group IIIA hydroxide gel and a polymeric cellulose ether compound to form a paste, (d) shaping the paste to form a shaped material, (e) calcining the shaped material to form a calcined material, (f) impregnating the calcined material with an aqueous solution of a Group VIII metal salt to provide the catalyst, and (g) calcining the catalyst.

9 Claims, 1 Drawing Sheet

U.S. PATENT DOCUMENTS

| | | | |
|---|---|---|---|
| 5,780,382 A | 7/1998 | Chang et al. | |
| 5,837,641 A | 11/1998 | Gosling et al. | |
| 5,854,170 A | 12/1998 | Chang et al. | |
| 6,080,904 A | 6/2000 | Chang et al. | |
| 6,326,328 B1 | 12/2001 | Matsuzawa | |
| 6,767,859 B2 | 7/2004 | Ying et al. | |
| 6,818,589 B1* | 11/2004 | Gillespie | 502/326 |
| 6,977,322 B2* | 12/2005 | Gillespie | 585/750 |
| 7,414,007 B2* | 8/2008 | Gillespie et al. | 502/208 |
| 2004/0059174 A1* | 3/2004 | Houzvicka et al. | 585/750 |
| 2004/0256289 A1* | 12/2004 | Gillespie et al. | 208/113 |
| 2005/0177009 A1* | 8/2005 | Levin et al. | 568/907 |
| 2005/0255994 A1* | 11/2005 | Houzvicka et al. | 502/308 |

OTHER PUBLICATIONS

G. Larsen et al., "A Study of Platinum Supported on Tungstated Zirconia Catalysts," Applied Catalysis A: General 139, 1996, pp. 201-211.

K. Arata et al., "Synthesis of Solid Superacid of Tungsten Oxide Supported on Zirconia and Its Catalytic Action," Proceedings 9th International Congress on Catalysis, vol. 4, 1988, pp. 1727-1735.

* cited by examiner

PROCESS FOR THE PREPARATION OF A PARAFFIN ISOMERIZATION CATALYST

This is a continuation-in-part of U.S. application Ser. No. 11/287,206, filed on Nov. 28, 2005, now abandoned the entire disclosure of which is incorporated by reference herein.

FIELD OF THE INVENTION

The present invention relates to the preparation of a paraffin isomerization catalyst comprising mixed aluminium and zirconium oxides modified with tungsten oxide and a hydrogenation/dehydrogenation component of a Group VIII metal. The catalyst is useful for the production of high-octane gasoline from a hydrocarbon feed stream comprising $C_{4+}$ hydrocarbon cuts.

BACKGROUND OF THE INVENTION

Multi-branched paraffins are ideal gasoline-blending components possessing high octane numbers. For environmental reasons, there is a need to find substitutes for aromatic components in gasoline. Therefore, there is an incentive to develop a process for increasing the octane number of the $C_4$-$C_{12}$ cuts. While $C_5$/$C_6$ paraffin isomerization is a common refinery process, commercialisation of processes including higher fractions ($C_{7+}$ hydrocarbons) meets significant difficulties given by the usually high degree of cracking to gaseous products, which is undesirable.

An article by K. Arata and M. Hino in Proceedings $9^{th}$ International Congress on Catalysis (1988, vol. 4, pages 1727-1735) describes a catalyst based on a Group IVB metal oxide such as zirconia in particular modified by an oxyanion of the Group VIB particularly tungstate and its use in paraffin isomerization.

Further research activities have shown that the catalytic performance of tungstated zirconia catalysts in paraffin isomerization may be improved by addition of a hydrogenation/dehydrogenation function, preferentially a noble metal, to the mixed solid acid catalysts. The use of tungstated zirconia promoted with noble metal in paraffin isomerization has been described in the open literature for instance by S. L. Soled, S. Miseo, J. E. Baumgartner, W. E. Gates, D. G. Barton and E. Iglesia, Proc. $13^{th}$ Int. Conf. Catal. (The Taniguchi Foundation, Kobe, Japan, 1994) page 17; E. Iglesia, D. G. Barton, S. L. Soled, S. Miseo, J. E. Baumgartner, W. E. Gates, G. A. Fuentes and G. D. Meitzner, Stud. Surf. Sci. Catal. 101 (1996) 533; G. Larsen, E. Lotero, S. Raghavan, R.D. Parra and C.A. Querini, Appl. Catal. A 139 (1996) 201.

A series of U.S. patents on solid acid isomerization catalysts have been assigned to Mobil Oil Corporation. U.S. Pat. No. 5,510,309 provides a method for preparing an acidic solid comprising a Group IVB metal oxide modified with an oxyanion of a Group VIB metal. An example of this acidic solid is zirconia modified with tungstate. This modified solid oxide may be used as a catalyst for example to isomerise $C_4$ to $C_8$ paraffins. The modified solid oxide is prepared by co-precipitating the Group IVB metal oxide along with the oxyanion of the Group VIB metal. After filtration, the co-precipitate is calcined at 825° C. U.S. Pat. No. 5,780,382 provides a method for preparing an acidic solid comprising a Group IVB metal oxide modified with an oxyanion of a Group VIB metal.

U.S. Pat. No. 5,854,170 describes the preparation of a noble metal containing an acidic solid catalyst by impregnation of a Group IVB metal hydroxide or hydrated oxide with an aqueous solution comprising an oxyanion of a Group VIB metal. The noble metal (preferentially Pt) may be added by co-impregnation with the oxyanion of the Group VIB metal or in a separate impregnation step.

U.S. Pat. No. 6,080,904 describes a $C_4$-$C_8$ isomerization process utilising an isomerization catalyst with a hydrogenation/dehydrogenation component (preferentially Pt) and with solid acid component comprising a Group IVB metal oxide modified with an oxyanion of a Group VIB metal.

In all the above-mentioned patents, aluminium is mentioned merely as a conventional matrix material such as alumina, silica-alumina and silica with preference given to silica.

The tungstated zirconia system has frequently been described as catalyst for $C_{5+}$ isomerization. The catalysts typically contain tungsten oxide in a concentration below 20 wt % and hydrogenation component is platinum. However, the catalytic selectivity towards isomerization delivered by these materials is not sufficient. The following patents are variations of the above-mentioned prior art.

U.S. Pat. No. 5,422,327 describes a catalyst composition of a Group VIII metal incorporated into a support consisting of zirconia, said support being further impregnated with a mixture of silica and tungsten oxide and its use in paraffin isomerization.

U.S. Pat. No. 5,648,589 claims a catalytic isomerization process comprising contacting a $C_{5+}$ feed under isomerization conditions with a catalyst composition consisting of a Group VIII metal and a zirconia support impregnated with tungsten oxide and silica.

U.S. Pat. No. 5,837,641 describes an isomerization reaction over tungstated zirconia and the promotional effect of water on this catalyst.

U.S. Pat. No. 6,767,859 describes an alkane isomerization process using a catalyst composition of a metallic oxide doped by a metal dopant, a Group IVB metal and a hydrogenation/dehydrogenation function, the metal-doped metallic oxide being prepared by co-precipitation from solution and the metal dopant being incorporated into the crystal lattice of the metallic oxide by calcination at sufficiently high temperatures. The metal dopant incorporation into the crystal lattice of the metallic oxide is verified by X-ray diffraction. This catalyst composition shows high activities towards alkane conversion but suffers from the disadvantage of a low selectivity towards alkane isomerization and a high cracking selectivity towards gaseous $C_1$-$C_4$ products with low commercial value.

The preparation of mechanically stable sulphated zirconia catalysts by addition of alumina is described in patent literature for example in U.S. Pat. No. 6,326,328.

When alumina is present in tungstated zirconia catalysts it may be incorporated in the zirconia crystal lattice as aluminium ion ($Al^{3+}$). Conventional catalysts in this form have been found to have a low selectivity to the isomerization products and tend to crack the multi-branched hydrocarbons produced to undesirable gaseous products.

The general objective of the invention is to provide a process for the preparation of a catalyst which is suitable for improving the octane number of a $C_{4+}$ hydrocarbon mixture through isomerization without substantial cracking of the produced multi-branched hydrocarbons to gaseous products.

It is another objective of the invention to provide a catalyst, which is suitable for improving the octane number of a $C_{4+}$ hydrocarbon mixture through isomerization without substantial cracking of the produced multibranched hydrocarbons to gaseous products.

It is a further objective of the invention to provide a catalyst, which contains reduced amounts of alumina while showing improved isomerization properties and reduced cracking properties.

BRIEF SUMMARY OF THE INVENTION

The above objective is achieved by process, whereby a paraffin isomerization catalyst is prepared, the catalyst comprising a combination of three oxides chosen from a Group IVB metal oxide, a Group VIB metal oxide and a Group IIIA metal oxide. The catalyst is useful for the production of high-octane gasoline from a hydrocarbon feed stream comprising $C_{4+}$ hydrocarbon cuts.

The invention comprises a process for preparation of a paraffin isomerization catalyst comprising a mixture of a Group IVB metal oxide, a Group VIB metal oxide, a Group IIIA metal oxide and a Group VIII metal, the process comprising the steps of (a) contacting a hydroxide of the Group IVB metal with an aqueous solution of an oxyanion of the Group VIB metal to provide a mixture,
(b) drying the mixture to provide a dry powder,
(c) kneading the dry powder with a Group IIIA hydroxide gel and a polymeric cellulose ether compound to form a paste,
(d) shaping the paste to form a shaped material,
(e) calcining the shaped material to form a calcined material,
(f) impregnating the calcined material with an aqueous solution of a Group VIII metal salt to provide the catalyst, and
(g) calcining the catalyst.

The invention concerns also a paraffin isomerization catalyst prepared by the above-mentioned process and comprising a Group IVB metal oxide, a Group VIB metal oxide, a Group IIIA metal oxide and a Group VIII metal, the catalyst having an X-ray powder diffraction (XRPD) 2θ range of less than 30.20°.

Finally, the invention concerns a method for the production of high-octane gasoline from a hydrocarbon feedstock comprising $C_{5+}$ hydrocarbon cuts, whereby the hydrocarbon feedstock is contacted with the above-mentioned paraffin isomerization catalyst.

DETAILED DESCRIPTION OF THE INVENTION

Figure 1:
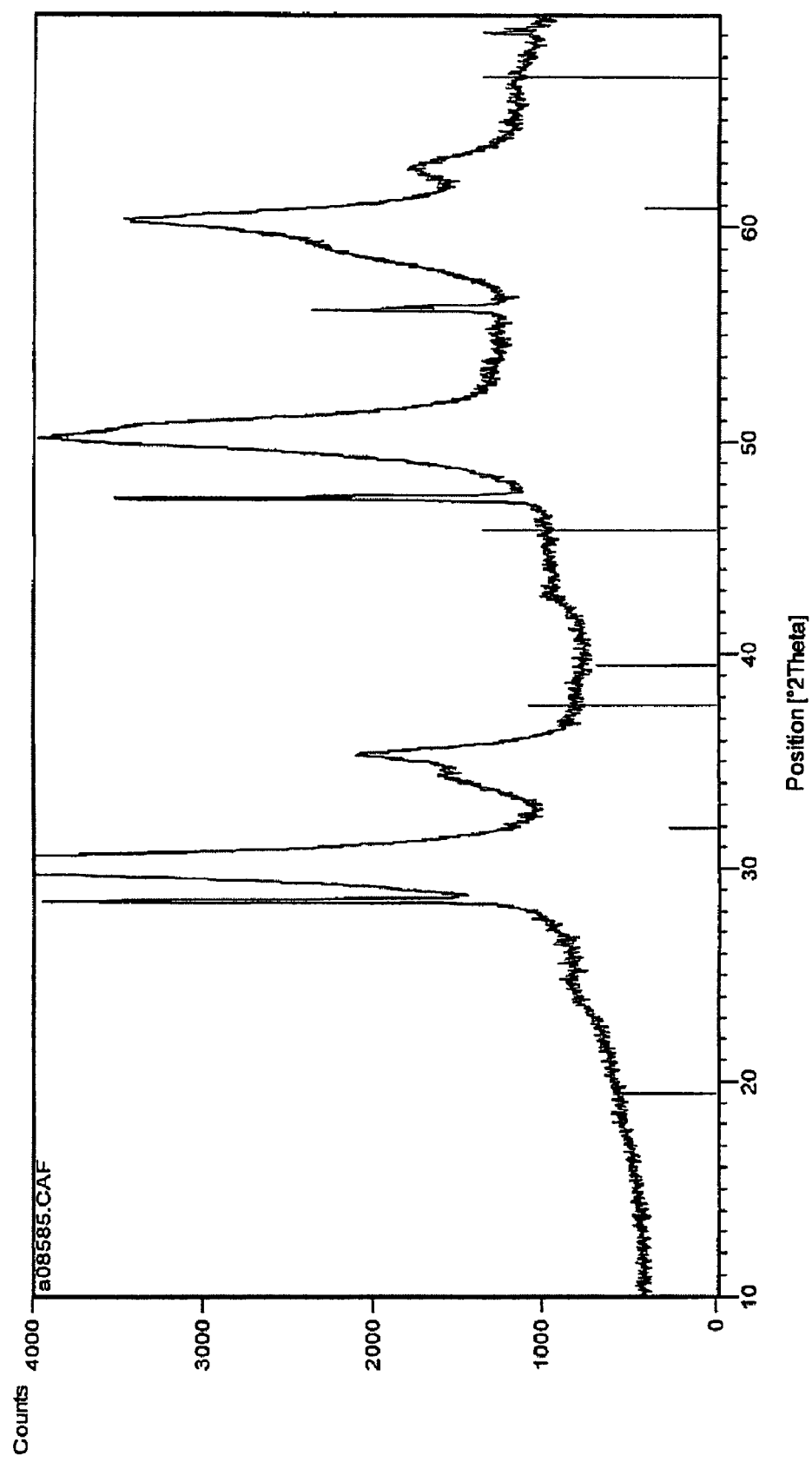
FIG. 1 shows a spectogram from X-ray analysis of a catalyst prepared according to one embodiment of the invention.

The catalyst prepared by the process of the invention is a solid acid catalyst suitable for improving the octane number of a $C_{4+}$ hydrocarbon mixture through isomerization without substantial cracking of the produced multibranched hydrocarbons to gaseous products.

Multi-branched isomers are in this case defined as compounds containing more than one carbon atom bonding to at least three other neighbouring carbon atoms or containing at least one carbon atom bonding to four neighbouring carbon atoms. Mono-branched isomers are defined as compounds containing just one carbon atom with bonds to three neighbouring carbon atoms.

The catalyst prepared according to the process of the invention can be applied to $C_{7+}$ fractions or cuts containing this fraction (e.g. $C_4$-$C_7$, $C_5$-$C_9$, $C_7$-$C_9$, $C_6$-$C_7$, $C_7$, $C_8$ or $C_9$, $C_7$-$C_{12}$) and consisting mainly of paraffins and possibly naphthenes, aromates and olefins.

The process of the invention has several advantages:
preparation of the catalyst is carried out using inexpensive raw materials thus providing economic advantages over catalyst preparations from halogenated starting materials.
use of metal halide containing starting materials is avoided thereby avoiding extensive procedures for the removal of halide anions from the catalyst material. The exclusion of halide anions on the catalyst material provides technical advantages, since this avoids corrosion problems in the technical equipment of the isomerization reactor units and increases catalyst lifetime.
the alumina content in the catalyst is low, while at the same time mechanically strong catalyst extrudates are provided.

The catalyst prepared according to the process of the invention comprises a carrier based on a combination of three oxides chosen from a Group IVB metal oxide, a Group VIB metal oxide and a Group IIIA metal oxide. The carrier is then impregnated with a Group VIII metal to provide the final catalyst.

The mixture of the Group IVB metal hydroxide with the aqueous solution of the Group VIB metal oxyanion can be dried by for instance spray drying or other drying processes. Shaping can be carried out by for instance extrusion or other shaping processes. The catalyst is calcined at a temperature sufficiently high to decompose the Group VIII metal salt.

In an embodiment of the invention, the spray dried mixture comprising oxides of Group IVB metal and Group VIB metal is pre-calcined at 600-800° C.

In a preferred embodiment of the invention, the catalyst prepared by the inventive process comprises zirconia, alumina and tungsten oxide, which are calcined and impregnated with a Group VIII metal.

In yet a preferred embodiment of the invention, the process for preparation of the catalyst comprises kneading the mixture of the zirconia, alumina and tungsten oxide with a polymeric cellulose ether compound to form a paste suitable for shaping followed by calcining and then impregnation with a Group VIII metal salt to provide a catalyst.

Polymeric cellulose ether compounds suitable for use in the process of the invention are obtained from cellulose substituted with substituents selected from the group of alkyl, carboxyl, hydroxyl and combinations thereof, and the alkyl substituents are selected from the group of methyl, ethyl, propyl and combinations thereof.

Preferable polymeric cellulose ether compounds are carboxyethyl cellulose, carboxymethyl cellulose, carboxymethyl hydroxyethyl cellulose, hydroxyethyl cellulose, hydroxypropyl cellulose, methylhydroxy propylcellulose, methyl cellulose, ethyl cellulose, propyl cellulose, ethyl carboxymethyl cellulose, methylethyl cellulose and hydroxyl propylmethyl cellulose.

Most preferably the polymeric cellulose ether compound is methyl cellulose.

In an embodiment of the invention the process is suitable for preparing a catalyst comprising mixed aluminium and zirconium oxides modified with tungsten oxide and a hydrogenation/dehydrogenation component of a Group VIII metal.

In the process of the invention calcination of the shaped material comprising the Group IVB metal hydroxide, the oxyanion of Group VIB metal and the Group IIIA metal simultaneously with a polymeric cellulose ether compound provides for a reduction in the amount of Group IIIA hydroxide gel to be used while contributing to the mechanical strength of the catalyst.

The polymeric cellulose ether compound is however not present in the catalyst obtained by the process of the invention as it is combusted during calcination. The catalyst differs from other conventional catalysts based on a Group IVB metal oxide, a Group VIB metal oxide, a Group IIIA metal oxide and a Group VIII metal in which the Group IIIA metal is incorporated in the crystal lattice of the Group IVB metal oxide. The catalyst obtained by the process of the invention does not have the Group IIIA metal incorporated in the Group IVB metal oxide crystal lattice, and it is characterised by having an X-ray powder diffraction 2θ value of less than 30.20°. This leads to the advantage of improved selectivity and activity for isomerization.

In an embodiment of the invention the X-ray diffraction 2θ value is 30.10° to less than 30.20°.

When carrying out X-ray powder diffraction measurements the position for the D[101] line for the Group IVB metal oxide is suitable for use as an indicator for the degree of incorporation of the Group IIIA metal. The incorporation of the Group IIIA metal (as $Al^{3+}$) leads to a decrease in the lattice parameters of the Group IVB metal oxide and hence to higher 2θ values.

In an embodiment of the invention calcination of the shaped material is carried out at a temperature of 600° C. to less than 800° C. Calcination at temperatures of 800° C. or above this temperature does not result in catalysts having X-ray powder diffraction 2θ values of less than 30.20°.

The calcination temperature for the mixed zircnium/tungsten/aluminium oxide carrier is also an important parameter for the activity and selectivity of the catalyst prepared by the process of the invention. Calcination at the temperature of 600° C. to less than 800° C. leads to a catalyst with a high selectivity towards isomerisation, thus providing significant economic advantages compared to state-of-the-art catalysts.

In a preferred embodiment of the invention calcination of the shaped material is carried out at a temperature of 625-700° C.

In an embodiment of the invention the polymeric cellulose ether compound is added in amounts of 0.1-5 wt % to the paste. Preferably amounts of 0.6-1.2 wt % are added.

In an embodiment of the invention the amount of Group IIIA metal oxide added is reduced to less than 10 wt % for instance to 2 wt %. For comparison, the amount of Group IIIA metal oxide can be as high as 22 wt % without the use of the polymeric cellulose ether compound.

The most typical aluminium source is hydrated aluminas like pseudoboehmite. Aluminium halides such as $AlCl_3 \cdot 6H_2O$ are preferably avoided because of their corrosive nature towards large scale steel equipment and their higher cost as compared to pseudoboehmite.

The quality of the Group IVB metal oxide is very important for the total catalyst performance. In an embodiment of the invention a group IVB metal oxide such as zirconium tetrahydroxide can be applied. Zirconium hydroxide can be prepared for example by precipitation of zirconyl nitrate with ammonia at high pH followed by heating under reflux similarly to A. Calafat, Stud. Surf. Sci. Catal. 118 (1998) 837. An example of zirconium hydroxide suitable for use in the process of the invention has a particle size of 10 μm and possessed a surface area above 300 m²/g.

In an embodiment of the invention the Group VIB metal oxide is an oxide of tungsten. The most typical tungsten precursor is ammonium metatungstate, which is useful due to its high solubility and low price.

The Group VIII metal may be selected from any of the Group VIII metals and mixtures thereof. The preferred metals are palladium and platinum with a concentration between 0.01 wt % to 5 wt %, most preferentially between 0.05 wt % to 1 wt %.

In an embodiment of the invention the catalyst prepared according to the inventive process comprises mixed aluminium and zirconium oxides modified with tungsten oxide and a hydrogenation/dehydrogenation component of a Group VIII metal, the process comprises the following steps:
(a) Spray drying a mixture of zirconium tetrahydroxide suspended in an aqueous solution of ammonium metatungstate to form a spray dried mixture and optionally pre-calcining the spray dried mixture at 650-700° C.,
(b) Kneading a mixture of pre-calcined spray dried product (zirconium and tungsten oxides/hydroxides) with alumina gel, pseudoboemite and methyl cellulose to a paste,
(c) Shaping the paste by extrusion to form an extrudate,
(d) Calcining the extrudate at 600-800° C., most preferentially at 625-700° C. to form the calcined material,
(e) Impregnation of the calcined material with the Group VIII metal to provide the catalyst,
(f) Calcination of the resulting catalyst at 300-500° C., preferentially between 350° C. to 450° C.

In an embodiment of the invention, the calcined catalyst comprises 10-50 wt % tungsten oxide, 2-40 wt % aluminium oxide and a remainder of zirconium oxide and the Group VIII metal.

The overall lower catalyst activity can be compensated for by increasing the temperature for the isomerization reaction. This increases the catalytic conversion without significantly increasing the cracking selectivity.

Typical operating conditions for the isomerization reaction are temperatures between 150-300° C., total pressures varying between 1 and 100 bar and liquid space velocities (LHSV) between 0.1 to 30 $h^{-1}$. The preferred conditions are temperatures between 130-250° C., LHSV of 0.5-5 $h^{-1}$, pressures between 5-50 bar and a hydrogen:hydrocarbon ratio between 0.1 and 5.

The feed may optionally also include shorter paraffins, aromatics or cycloparaffins. When passing such a feed through the reactor bed, shorter paraffins are also isomerised, while aromatics are hydrogenated to the corresponding cycloalkanes. The reaction rate for ring opening will typically be very slow.

Specific embodiments of the invention for the production of a high liquid yield of gasoline with a high research octane number (RON) are described in more detail below.

The selectivity is defined as the ratio between the sum of the weight of the isomers 2,2-dimethylpentane (2,2-DMP), 2,4-dimethylpentane (2,4-DMP) and 2,2,3-trimethylbutane (2,2,3-TMB) and the sum of the weight of all products.

The cracking factor is defined as the ratio between the sum of the weight of gaseous products ($C_1$-$C_4$) and the sum of the weight of the isomers 2,2-dimethylpentane (2,2-DMP), 2,4-dimethylpentane (2,4-DMP) and 2,2,3-trimethylbutane (2,2,3-TMB). During the X-ray powder diffraction measurements the position for the D[101] line for tetragonal zirconia was used as an indicator for the degree of incorporation of aluminium.

EXAMPLES

Example 1

Spray drying of zirconium hydroxide and ammonium metatungstate was carried out as follows:

12.0 kg $(NH_4)_6H_6W_{12}O_{40}$ were dissolved in 180 liter demineralised water. 28.0 kg $Zr(OH)_4$ were mixed with the solution. The mixture was dried in a spray drier with an inlet temperature of 250° C., an outlet temperature of 90° C. and a feed flow of 29 kg/h.

Example 2

Comparative Example

Preparation of an isomerization catalyst with 22 wt % of alumina:

1.432 kg of the spray dried product obtained in Example 1 were mixed with 1.400 kg alumina gel (pseudoboemite 30%) and 112 g pseudoboemite powder for 10 min and extruded as 1/16" cylinders. The extrudates were dried at 110° C. over night and calcined at 650° C. for 3 h 0.5 wt % Pd was introduced by incipient wetness impregnation of an aqueous $[Pd(NH_3)_4](NO_3)_2$ solution. The thus obtained catalyst was calcined at 400° C. for 6 h in a flow of air (4 l/min·kg catalyst) before it was placed into the reactor. Catalytic isomerization:

Prior to the catalytic isomerization experiment, the catalyst was reduced with $H_2$ (200 Nml/min) at 200° C. and atmospheric pressure. Heptane isomerization with the catalyst prepared in Example 2 was performed in a fixed-bed reactor at a total pressure of 6 atm and with a LSHV of 2.03 $h^{-1}$. The feed consisted of a hydrogen/heptane mixture with a molar ratio of 4.95:1. Catalytic results are shown in Table 1.

Example 3

Comparative Example:

To 52.7 g zirconyl chloride ($ZrOCl_2 \cdot 8H_2O$, 30% solution in hydrochloric acid) were added concentrated $NH_4OH$(aq) until the solution pH was approximately 9. The resulting slurry, $Zr(OH)_4$, was filtered and washed with 500 g of distilled, deionized water. The solid was air-dried at 130° C. for 16 hours. The dried product (11.9 g) was impregnated via incipient wetness with 8.9 g of an aqueous solution containing 2.12 g of ammonium metatungstate, $(NH_4)_6H_6W_{12}O_{40}$. The resulting material was dried in air and then calcined at 825° C. in air for 3 hours 7.0 g of the dried product were impregnated by incipient wetness by an aqueous solution of 55 mg $(NH_4)_2PdCl_4$. The catalyst was then dried at 300° C. in air for 2 hours.

Catalytic Isomerization Test (Comparative):

Prior to the catalytic experiment, the catalyst was reduced with $H_2$ (200 Nml/min) at 200° C. and atmospheric pressure. Heptane isomerization with the catalyst prepared in Example 6 was performed in a fixed-bed reactor at a total pressure of 6 atm and with a LSHV of 1.14 h−1. The feed consisted of a hydrogen/hydrocarbon mixture with a molar ratio of 4.41:1. Catalytic results are shown in Table 1.

Example 4

Comparative Example:

0.161 mol of $ZrOCl_2 \cdot 8H_2O$ was mixed with 0.0082 mol of $AlCl_3 \cdot 6H_2O$ in a 600 ml glass beaker. 320 ml of $H_2O$ were added to dissolve the salts with stirring. Then 25% $NH_4OH$ were added dropwise to the solution under vigorous stirring until the final pH of the precipitation mixture reached 9.0. After stirring for more than 1 hour, the precipitate was washed by distilled water and recovered through centrifugation. The material was washed 6 times to remove the chloride ions. The precipitate was dried in an oven at 120° C. over night. Then, an aqueous solution of ammonium metatungstate (3.13 g) was added to the mixed hydroxide via the incipient wetness technique. After calcination at 800° C. for 3 hours, the tungstated $Al^{3+}$ doped zirconia obtained was impregnated with 0.5 wt % Pd using an aqueous $[Pd(NH_3)_4](NO_3)_2$ solution. The catalyst was calcined at 450° C. for 3 hours before it was placed into the reactor.

Catalytic Isomerization Test:

Prior to the catalytic experiment, the catalyst was reduced with $H_2$ (200 Nml/min) at 200° C. and atmospheric pressure. Heptane isomerization with the catalyst prepared according to Example 8 was performed in a fixed-bed reactor at a total pressure of 6 atm and with a LSHV of 2.14 $h^{-1}$. The feed was consisting of a hydrogen/hydrocarbon mixture with a molar ratio of 4.93:1. Catalytic results are shown in Table 1.

The selectivity to 2,2-DMP, 2,4-DMP and 2,2,3-TMB in wt % was measured in all the tests.

TABLE 1

| Comparative examples: | $Al_2O_3$ content, (wt %) | Calcination temperature, (° C.) | 2θ [101] $ZrO_2$ (°) | Temp., (° C.) | $C_7$ Conversion, (%) | Cracking factor, (%) | Selectivity, (wt %) |
|---|---|---|---|---|---|---|---|
| 2 | 22 | 650 | 30.24 | 200.00 | 59.8 | 5.2 | 6.55 |
| 3 | 0 | 825 | — | 230.00 | 7.9 | 23.8 | 0.09 |
| 4 | 3.2 | 800 | 30.289 | 165.0 | 27.2 | 9.8 | 2.38 |
| 4 | 3.2 | 800 |  | 178.0 | 51.9 | 13.2 | 6.30 |
| 4 | 3.2 | 800 |  | 205.0 | 88.3 | 38.2 | 18.96 |

The results given in Table 1 show the dependence of the catalytic $C_7$ conversion and the cracking factor on the carrier calcination temperature. The lower the temperature, the lower is the catalytic $C_7$ conversion and the lower is the cracking factor.

It can also be seen that at increase in calcination temperature from 650° C. to 800° C. results in incorporation of aluminium in the zirconia lattice.

The results of Example 2 indicate that despite the low calcination temperature of 650° C. aluminium is incorporated in the zirconia lattice, since it is present in a high amount (22 wt %).

Comparative Example 4 shows that when a conventional process is used aluminium is incorporated in the zirconia lattice even when very low amounts of alumina are used (3.2 wt %).

Example 5

Preparation of an isomerisation catalyst using a polymeric cellulose ether compound.

167.6 g of the spray dried product obtained in Example 1 were mixed with 33.4 g alumina gel (pseudoboemite 30%), 3.0 g methyl cellulose and 68 g water. The paste was extruded as 1/16" cylinders. The extrudates were dried at 110° C. for 6 hours and calcined at 650° C. for 1 hour on a net. 0.5 wt % Pd was introduced by incipient wetness impregnation of an aqueous $[Pd(NH_3)_4](NO_3)_2$ solution. The thus obtained catalyst was calcined at 400° C. for 6 hours in a flow of air (4 l/min·kg catalyst) before it was placed into the reactor.

Prior to the catalytic isomerization experiment, the catalyst was reduced with $H_2$ (200 Nml/min) at 200° C. and atmospheric pressure. Heptane isomerization with the catalyst was performed in a fixed-bed reactor at a total pressure of 20 atm and with a LSHV of 2.03 $h^{-1}$. The feed consisted of a hydrogen/heptane mixture with a molar ratio of 2.2:1. Catalytic test results are shown in Table 2.

The X-ray diffraction diagram is shown in FIG. 1. It can be seen that the 2 theta (2θ) zirconia peak is shifted to below 30.2° indicating that aluminium is not incorporated in the zirconia crystal lattice and that aluminium is found primarily in the amorphous from outside the zirconia crystal lattice.

Example 6

Preparation of an isomerisation catalyst using a polymeric cellulose ether compound.

335.2 g of the spray dried product obtained in Example 1 were mixed with 66.8 g alumina gel (pseudoboemite 30%), 6.0 g methyl cellulose and 130 g water. The paste was extruded as 1/16" cylinders. The extrudates were dried at 110° C. for 6 hours and calcined at 650° C. for 3 hours in an open container with 5 cm extrudate bed height. 0.5 wt % Pd was introduced by incipient wetness impregnation of an aqueous [Pd(NH$_3$)$_4$] (NO$_3$)$_2$ solution. The thus obtained catalyst was calcined at 400° C. for 6 hours in a flow of air (4 l/min·kg catalyst) before it was placed into the reactor.

Prior to the catalytic isomerization experiment, the catalyst was reduced with H$_2$ (200 Nml/min) at 200° C. and atmospheric pressure. Heptane isomerization with the catalyst was performed in a fixed-bed reactor at a total pressure of 20 atm and with a LSHV of 2.14 h$^{-1}$. The feed consisted of a hydrogen/heptane mixture with a molar ratio of 2.1:1. Catalytic test results are shown in Table 2.

TABLE 2

| Example: | 2θ [101] ZrO$_2$ (°) | Temperature (° C.) | C$_7$ conversion (%) | Cracking factor (%) | Selectivity (%) |
|---|---|---|---|---|---|
| 5 | 30.183 | 209.6 | 43.5 | 4.5 | 3.13 |
|   |        | 220.4 | 61.4 | 7.2 | 6.88 |
|   |        | 225.9 | 74.4 | 10.3 | 11.19 |
| 6 | 30.18  | 200.0 | 68.8 | 13.0 | 8.66 |

From the results it can be seen that 2θ values lower than 30.2° are obtained indicating that aluminium is not incorporated into the zirconia crystal lattice.

What is claimed is:

1. Process for preparation of a paraffin isomerization catalyst comprising a mixture of a zirconium oxide, a Group VIB metal oxide, aluminum oxide and a Group VIII metal, the process comprising the steps of:
   (a) contacting a hydroxide of zirconium with an aqueous solution of an oxyanion of the Group VIB metal to provide a mixture;
   (b) drying the mixture to provide a dry powder;
   (c) kneading the powder with an aluminum hydroxide gel and a polymeric cellulose ether compound to form a paste, the amount of aluminum hydroxide added being less than 10 wt %;
   (d) shaping the paste to form a shaped material;
   (e) calcining the shaped material to form a calcined material;
   (f) impregnating the calcined material with an aqueous solution of a Group VIII metal salt to provide the catalyst; and
   (g) calcining the catalyst to obtain a paraffin isomerisation catalyst having an x-ray powder diffraction (XRPD) reflection 2θ range of less than 30.20' for tetragonal zirconia.

2. Process according to claim 1, wherein the polymeric cellulose ether compound is obtained from cellulose substituted with substituents selected from the group of alkyl, carboxyl, hydroxyl and combinations thereof, and the alkyl substituents are selected from the group of methyl, ethyl, propyl and combinations thereof.

3. Process according to claim 2, wherein the polymeric cellulose ether compound is selected from the group consisting of carboxyethyl cellulose, carboxymethyl cellulose, carboxymethyl hydroxyethyl cellulose, hydroxyethyl cellulose, hydroxypropyl cellulose, methylhydroxy propylcellulose, methyl cellulose, ethyl cellulose, propyl cellulose, ethyl carboxymethyl cellulose, methylethyl cellulose and hydroxyl propylmethyl cellulose.

4. Process according to claim 1, wherein the dry powder is pre-calcined before kneading.

5. Process according to claim 1, wherein the shaped material is calcined at a temperature of 600-800° C.

6. Process according to claim 1, wherein the Group VIB metal is tungsten, and the polymeric cellulose ether is methyl cellulose.

7. Process according to claim 1, wherein the calcined catalyst comprises 10-50 wt % tungsten oxide, 2-10 wt % aluminum oxide and a remainder of zirconium oxide and the Group VIII metal.

8. Process according to claim 1, wherein the Group VIII metal is palladium and/or platinum in an amount of 0.01-5 wt %.

9. Paraffin isomerization catalyst prepared by the process of claim 1, comprising a mixture of a zirconium oxide, a Group VIB metal oxide, less than 10 wt % of an aluminum oxide and a Group VIII metal, the catalyst having an X-ray powder diffraction (XRPD) reflection 2θ range of less than 30.20° for tetragonal zirconia.

* * * * *